United States Patent
Lee et al.

(10) Patent No.: US 10,092,474 B2
(45) Date of Patent: Oct. 9, 2018

(54) SUPPORTING FRAME AND MOTION ASSISTANCE APPARATUS INCLUDING THE SAME

(71) Applicant: Samsung Electronics Co., Ltd., Suwon-Si, Gyeonggi-Do (KR)

(72) Inventors: Youn Baek Lee, Yongin-si (KR); Byungjune Choi, Gunpo-si (KR); Hyun Do Choi, Yongin-si (KR); Jeonghun Kim, Hwaseong-si (KR); Se-Gon Roh, Suwon-si (KR); Minhyung Lee, Anyang-si (KR); Jongwon Lee, Uiwang-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 837 days.

(21) Appl. No.: 14/596,719

(22) Filed: Jan. 14, 2015

(65) Prior Publication Data

US 2016/0015589 A1  Jan. 21, 2016

(30) Foreign Application Priority Data

Jul. 17, 2014 (KR) ........................ 10-2014-0090309

(51) Int. Cl.
*A61H 1/02* (2006.01)
*A61F 5/01* (2006.01)
*A61H 3/00* (2006.01)

(52) U.S. Cl.
CPC ............. *A61H 1/0262* (2013.01); *A61F 5/01* (2013.01); *A61H 1/024* (2013.01); *A61H 1/0244* (2013.01); *A61H 3/00* (2013.01); *A61H 2201/0192* (2013.01); *A61H 2201/1215* (2013.01); *A61H 2201/165* (2013.01);
(Continued)

(58) Field of Classification Search
CPC ........ A61H 1/0262; A61H 3/00; A61H 3/008; A61H 2003/007; A61H 2201/0192–2201/0196; A61H 2201/12–2201/1246; A61H 2201/1628–2201/163; A61H 2201/164–2201/165; A61H 2201/5061–2201/5069; A61H 2201/0406;
(Continued)

(56) References Cited

U.S. PATENT DOCUMENTS 4,557,150 A * 12/1985 Utsunomiya ........ G01G 3/1412
                                                        177/211
2007/0010772 A1* 1/2007 Ryan ..................... A61F 5/0123
                                                        602/26
(Continued)

FOREIGN PATENT DOCUMENTS

JP      3917432 B2    5/2007
JP      4112543 B2    7/2008
(Continued)

*Primary Examiner* — Rachel T Sippel
(74) *Attorney, Agent, or Firm* — Harness, Dickey & Pierce, P.L.C.

(57) ABSTRACT

A supporting frame and a motion assistance apparatus including the same may be provided. In particular, the supporting frame including a first frame including a hinge connecting portion, a second frame configured to slidingly move with respect to the first frame, and an assistance force sensing portion on at least one of the first frame and the second frame may be provided.

20 Claims, 11 Drawing Sheets

(52) U.S. Cl.
CPC ............. *A61H 2201/1628* (2013.01); *A61H 2201/1635* (2013.01); *A61H 2201/5061* (2013.01); *A61H 2201/5069* (2013.01)

(58) Field of Classification Search
CPC ........ A61F 5/01; A61F 5/0123–5/0125; A61F 2005/0132–2005/0188
See application file for complete search history.

(56) References Cited

U.S. PATENT DOCUMENTS

| | | | |
|---|---|---|---|
| 2012/0271207 A1* | 10/2012 | Schoen | A61F 5/0102 601/34 |
| 2013/0102934 A1* | 4/2013 | Ikeuchi | A61H 3/00 601/35 |
| 2013/0178775 A1* | 7/2013 | Paaske | A61F 5/0193 602/23 |
| 2013/0261513 A1 | 10/2013 | Goffer et al. | |
| 2013/0331744 A1* | 12/2013 | Kamon | A61H 3/00 601/35 |
| 2014/0121574 A1 | 5/2014 | Chladek | |

FOREIGN PATENT DOCUMENTS

| | | |
|---|---|---|
| JP | 4417300 B2 | 2/2010 |
| JP | 2012135486 A | 7/2012 |
| JP | 5381876 B2 | 1/2014 |
| JP | 2014068869 A | 4/2014 |
| KR | 100651638-BI | 11/2006 |
| KR | 100975557 B1 | 8/2010 |
| KR | 101350334 B1 | 1/2014 |

\* cited by examiner

SUPPORTING FRAME AND MOTION ASSISTANCE APPARATUS INCLUDING THE SAME

CROSS-REFERENCE TO RELATED APPLICATION

This application claims priority under 35 U.S.C. § 119 to Korean Patent Application No. 10-2014-0090309, filed on Jul. 17, 2014, in the Korean Intellectual Property Office, the disclosure of which is incorporated herein by reference in its entirety.

BACKGROUND

1. Field

Example embodiments relate to supporting frames and motion assistance apparatuses including the same.

2. Description of the Related Art

With the onset of rapidly aging societies, a number of people are experiencing inconvenience and/or pain from joint problems. Thus, there is a growing interest in motion assistance apparatuses enabling the elderly and/or patients having joint problems to walk with less effort. Furthermore, motion assistance apparatuses increasing muscular strength of human bodies are desired for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

The motion assistance apparatuses may include active joint structures including hydraulic systems and/or driving motors to drive each joint portion to improve muscular strength of legs of the users. For example, two motors to transmit driving power may be provided at both hip joint portions, respectively.

SUMMARY

According to an example embodiment, a supporting frame includes a first frame including a hinge connecting portion, a second frame provided configured to slidingly move with respect to the first frame, and an assistance force sensing portion on at least one of the first frame and the second frame.

In some example embodiments, a slidingly moving direction of the second frame may intersect a hinge axis of the hinge connecting portion of the first frame.

In some example embodiments, the assistance force sensing portion may include a first strain gauge disposed lengthwise in the slidingly moving direction of the second frame.

In some example embodiments, the assistance force sensing portion may include at least one pair of the first strain gauge and a second strain gauge disposed on an upper side and a lower side of the at least one of the first frame and the second frame, respectively.

In some example embodiments, the at least one cross-section of the first frame and the second frame taken in a direction of a hinge axis of the hinge connecting portion may be elongated in the direction of the hinge axis of the hinge connecting portion.

In some example embodiments, the assistance force sensing portion may include a strain gauge disposed on the at least one of the first frame and the second frame, and a portion of the at least one of the first frame and the second frame, on which the strain gauge is disposed, may have a cross-sectional area in the direction of the hinge axis smaller than that of a remaining portion of the at least one of the first frame and the second frame.

In some example embodiments, the at least one of the first frame and the second frame may include a deformed recess defined therein to accommodate the strain gauge.

In some example embodiments, the second frame may include a second guide portion configured to slidingly couple to a first guide portion of the first frame, an extending portion extending from the second guide portion, and an applying portion extending from the extending portion and configured to transmit an assistance force to an object.

In some example embodiments, the applying portion may include a face orthogonal to a hinge axis of the hinge connecting portion.

In some example embodiments, the applying portion may include a face parallel to a slidingly moving direction of the first guide portion and the second guide portion.

In some example embodiments, the applying portion may include a face orthogonal to a face of the second guide portion.

In some example embodiments, the extending portion may have a shape of being twisted at 90 degrees from the second guide portion to the applying portion on an axis corresponding to the slidingly moving direction of the first guide portion and the second guide portion.

According to an example embodiment, a supporting frame for transmitting power to an object includes a first frame including a hinge connecting portion, the hinge connecting portion configured to rotate on an axis corresponding to a power transmitting direction of the supporting frame, a second frame configured to slidingly move with respect to the first frame in a direction intersecting the power transmitting direction, and a tensile force measuring sensor on at least one of the first frame and the second frame.

In some example embodiments, the supporting frame may include a plurality of tensile force measuring sensors, which including the tensile force measuring sensor, and at least one pair of the plurality of tensile force measuring sensors may be disposed to face each other in the power transmitting direction.

In some example embodiments, the plurality of tensile force measuring sensors may include two pairs of tensile force measuring sensors disposed to face each other in the power transmitting direction.

In some example embodiments, the at least one of the first frame and the second frame may include a deformation resistant rib provided to prevent or mitigate a deformation of the at least one of the first frame and the second frame.

In some example embodiments, the deformation resistant rib may include a deformed recess defined therein, and the tensile force measuring sensor may be disposed to overlap the deformed recess in the power transmitting direction.

According to an example embodiment, a motion assistance apparatus includes a fixing member configured to be fixed to an object, a driving module on one side of the fixing member, a joint member rotatably connected to the fixing member and configured to be driven by the driving module, a first frame rotatably coupled to the joint member, a second frame configured to slidingly coupled to the first frame, a supporting member coupled to the second frame to support a portion of the object, and a tensile force measuring sensor on one of the first frame and the second frame.

In some example embodiments, an axis of rotation of the first frame may be orthogonal to an axis of rotation of the joint member.

In some example embodiments, a slidingly moving direction of the first frame and the second frame may be orthogonal to an axis of rotation of the joint member.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
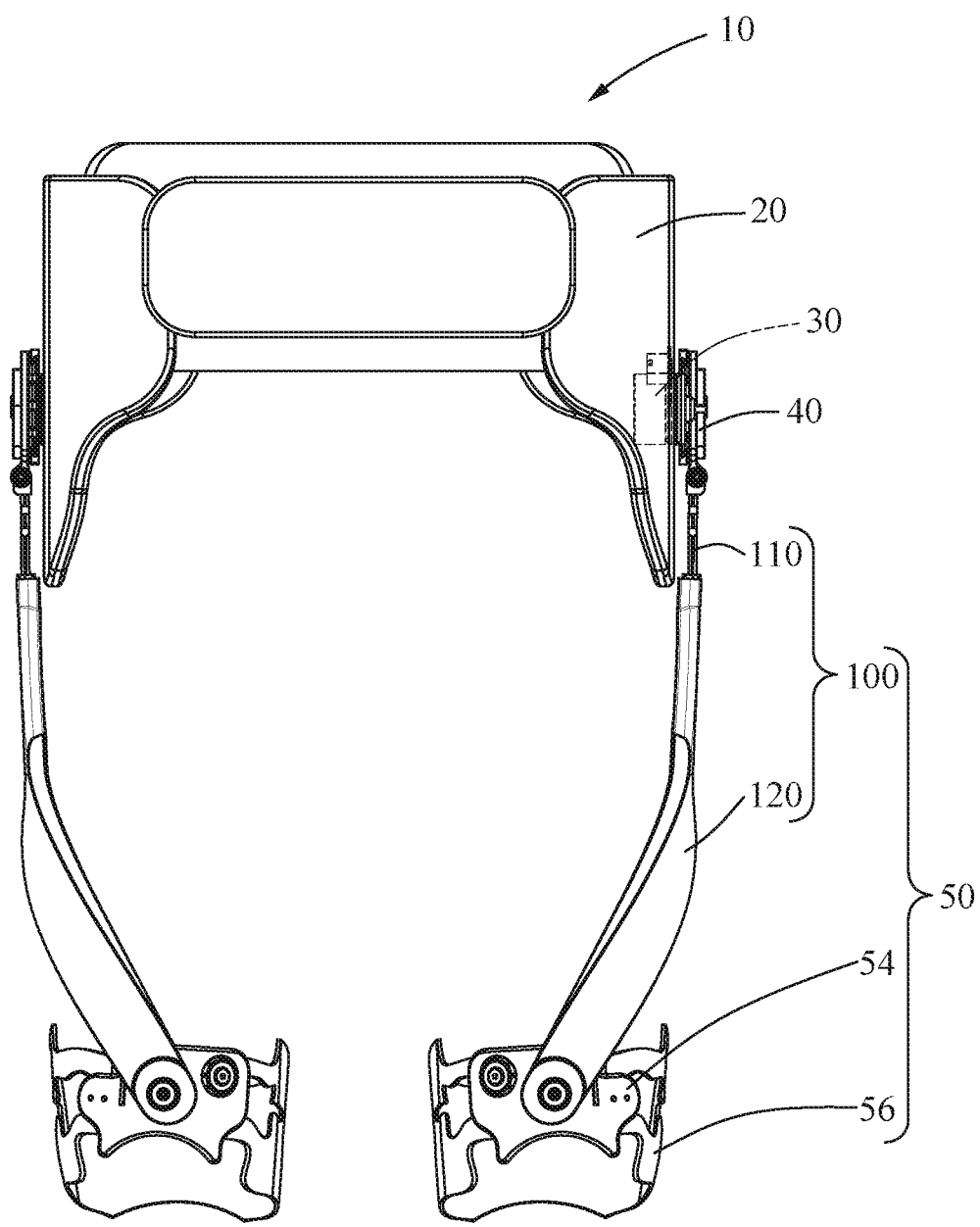
FIG. 1 is a front view illustrating a motion assistance apparatus according to example embodiments.

Hereinafter, various example embodiments will be described in detail with reference to the accompanying drawings. The present disclosure may, however, be embodied in many different forms and should not be construed as limited to the example embodiments set forth herein. Rather, these example embodiments are merely provided so that this disclosure will be thorough and complete, and will fully convey the scope of example embodiments to those skilled in the art. In the drawings, the sizes and relative sizes of the various layers and regions may have been exaggerated for clarity. Like numerals refer to like elements throughout. Thus, regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed appropriate.

In addition, terms such as first, second, A, B, (a), (b), and the like may be used herein to describe components of the present invention. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, some example embodiments will be explained in further detail with reference to the accompanying drawings.

Figure 2:
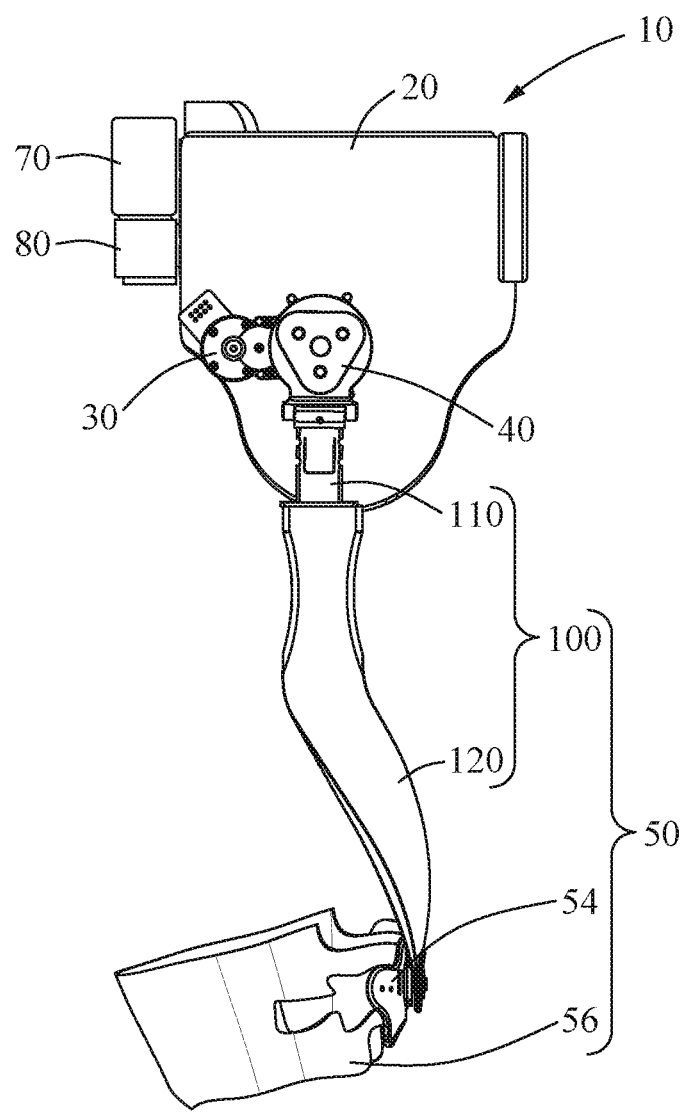
FIG. 2 is a side view illustrating a motion assistance apparatus according to example embodiments.

FIG. 1 is a front view illustrating a motion assistance apparatus 10 according to example embodiments, and FIG. 2 is a side view illustrating the motion assistance apparatus 10 according to example embodiments.

Referring to FIGS. 1 and 2, the motion assistance apparatus 10 may be worn on an object to assist a motion of the object. The object may be, for example, a human, an animal, or a robot. However, the object is not limited thereto. Further, although FIG. 1 illustrates a case in which the motion assistance apparatus 10 assists a motion of a thigh of the object, the motion assistance apparatus 10 may also assist a motion of another part of an upper body, for example, a hand, an upper arm, and a lower arm of the object, or a motion of another part of a lower body, for example, a foot, and a calf of the object. The motion assistance apparatus 10 may assist a motion of a part of the object. Hereinafter, a case in which the motion assistance apparatus 10 assists a motion of a thigh of a human will be described as examples.

The motion assistance apparatus 10 includes a fixing member 20, a driving module 30, a joint member 40, a supporting module 50, a controller 70 to control the driving module 30, and a power supply 80 to supply power to the driving module 30.

The fixing member 20 may be attached or coupled to the object. The fixing member 20 may be in contact with at least a portion of an outer surface of the object. The fixing member 20 may be formed to cover the outer surface of the object. The fixing member 20 may have a curved shape corresponding to a contact portion of the object. The fixing member 20 may include a curved surface to be in contact with the object. For example, the fixing member 20 may be attached or coupled to one side of a waist of the object.

The driving module 30 may provide power to the joint member 40. The driving module 30 may include a motor to receive a voltage or a current from the power supply 80 and generate power. For example, the driving module 30 may be disposed in a lateral direction of the joint member 40. An axis of rotation of the driving module 30 and an axis of rotation of the joint member 40 may be disposed to be spaced apart from each other. Accordingly, a height at which the motion assistance apparatus 10 externally protrudes from the object may be reduced compared to a case in which the driving module 30 and the joint member 40 are disposed to share an axis of rotation. The driving module 30 may be disposed to be spaced apart from the joint member 40. A power transmitting module may be provided to transmit power from the driving module 30 to the joint member 40. The power transmitting module may be a rotating body (e.g., a gear) or a longitudinal direction member (e.g., a wire, a cable, a string, a rubber band, a spring, a belt, and a chain). However, a position and a power transmitting structure of the driving module 30 are not limited to the example embodiments described herein.

The joint member 40 may receive power from the driving module 30 and assist a motion of a joint portion of the object. The joint member 40 may be disposed at a position corresponding to the joint portion of the object. The joint member 40 may be disposed on one side of the fixing member 20. One side of the joint member 40 may be connected to the driving module 30, and another side of the joint member 40 may be connected to the supporting module 50. The joint member 40 may rotate by the power received from the driving module 30. An encoder (not shown) may be disposed on one side of the joint member 40 to measure an angle of rotation of the joint member 40.

The supporting module 50 may support a portion of the object. The supporting module 50 may assist a motion of the portion of the object. The supporting module 50 may rotate by a torque of the joint member 40. The supporting module 50 includes an applying member 54, a supporting member 56, and a supporting frame 100.

The supporting frame 100 may transmit an "assistance force" to assist a motion of a portion of the object. The "assistance force" may refer to a force applied in a direction matching a motion direction of the portion of the object. The assistance force may be a force excluding a force applied in a direction intersecting the motion direction of the portion of the object from a force applied to the portion of the object. One end portion of the supporting frame 100 may be rotatably connected to the joint member 40. Another end portion of the supporting frame 100 may be connected to the supporting member 56 to transmit the assistance force to the portion of the object. For example, the supporting frame 100 may push or pull the thigh of the object. The supporting frame 100 may extend in a longitudinal direction of the thigh of the object. The supporting frame 100 may be bent to cover at least a portion of a circumference of the thigh of the object.

The applying member 54 may apply the assistance force to a portion of the object. The applying member 54 may be disposed between the other end portion of the supporting frame 100 and the supporting member 56. For example, the applying member 54 may be disposed on one side of the thigh of the object to push or pull the thigh of the object. The applying member 54 may be disposed on a front surface of the thigh of the object. The applying member 54 may be disposed along the circumference of the thigh of the object. The applying member 54 may extend from the other end portion of the supporting frame 100. The applying member 54 may include a curved surface having a shape corresponding to the thigh of the object.

The supporting member 56 may be connected to one side of the applying member 54. For example, the supporting member 56 may be disposed to cover a circumference of at least a portion of the thigh of the object, thereby preventing or mitigating a separation of the thigh of the object from the supporting frame 100.

Figure 3:
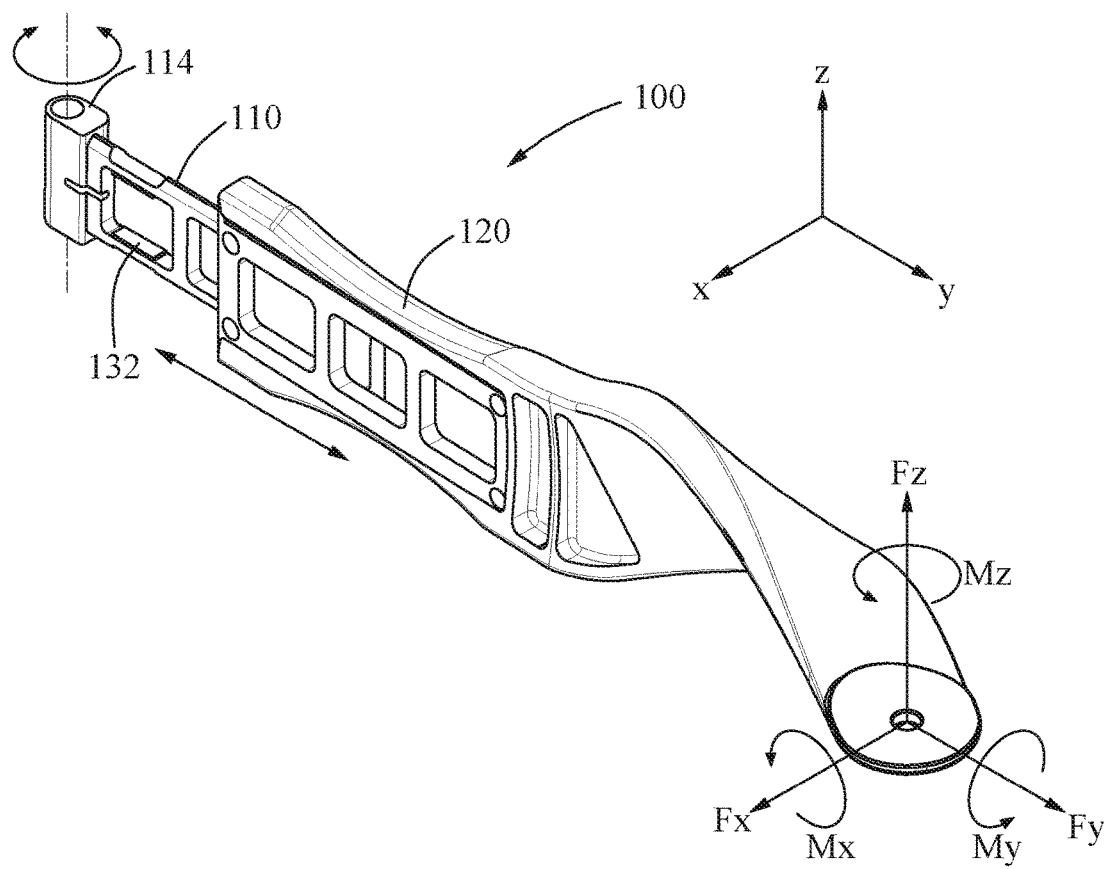
FIG. 3 is a perspective view illustrating a supporting frame according to example embodiments.
Figure 4:
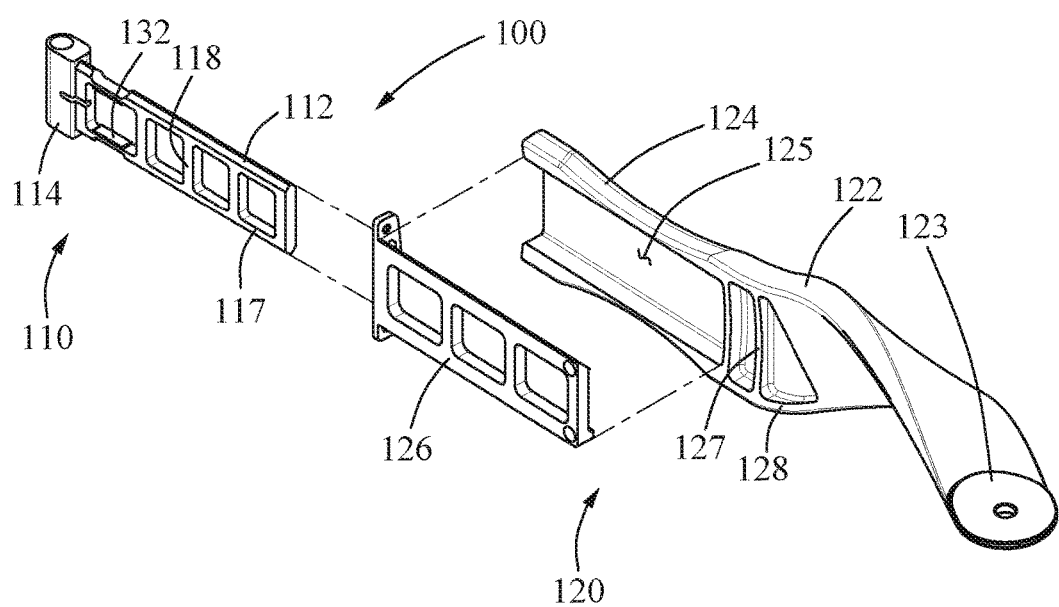
FIG. 4 is an exploded perspective view illustrating a supporting frame according to example embodiments.

FIG. 3 is a perspective view illustrating the supporting frame 100 according to example embodiments, and FIG. 4 is an exploded perspective view illustrating the supporting frame 100 according to example embodiments.

Figure 5:
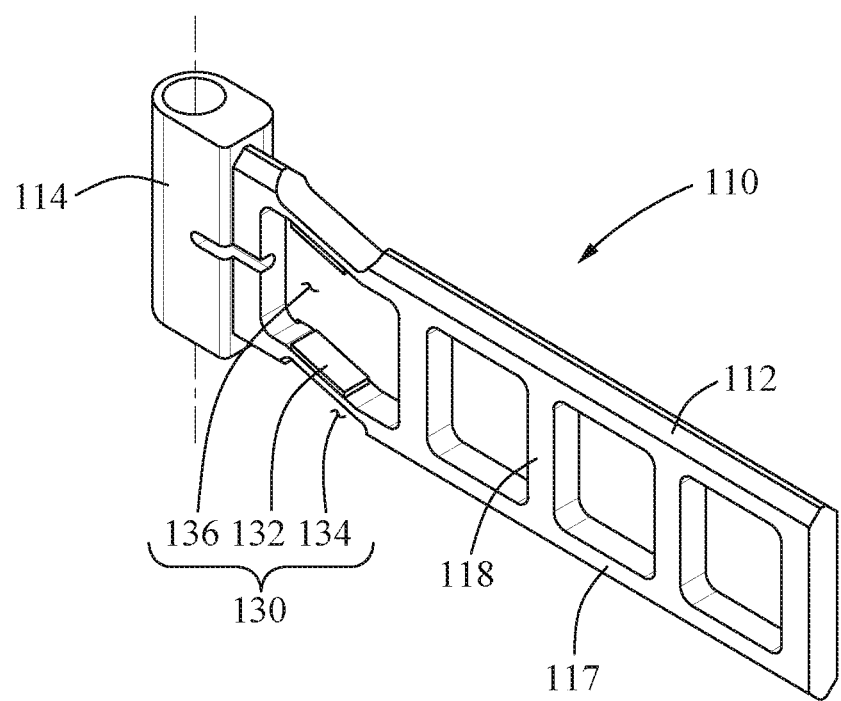
FIG. 5 is a perspective view illustrating a deformation of a supporting frame according to example embodiments.

Referring to FIGS. 3 and 4, the supporting frame 100 includes a first frame 110, a second frame 120, and an assistance force sensing portion 130 of FIG. 5.

The first frame 110 may be coupled or connected to the joint member 40 and the second frame 120. The first frame 110 includes a first guide portion 112, a hinge connecting portion 114, and first ribs 117 and 118. A cross-section of the first frame 110 taken in a direction of a hinge axis of the hinge connecting portion 114 may be elongated in the direction of the hinge axis of the hinge connecting portion 114.

The hinge connecting portion 114 may connect the first guide portion 112 to the joint member 40 of FIG. 2. The hinge connecting portion 114 may be disposed at one end of the first frame 110. The hinge connecting portion 114 may be rotatably connected to the joint member 40. A hinge axis of the hinge connecting portion 114 may intersect an axis of rotation of the joint member 40. For example, the hinge axis of the hinge connecting portion 114 may be orthogonal to the axis of rotation of the joint member 40. By means of the hinge connecting portion 114, the supporting frame 100 may perform an abduction or an adduction. The hinge connecting portion 114 may function as a passive joint that enables a rotary motion.

The first guide portion 112 may be slidingly coupled or connected to the second frame 120. The first frame 110 may be in surface contact with a portion of the object. The first guide portion 112 may be elongated in a direction intersecting the hinge axis of the hinge connecting portion 114.

The first ribs 117 and 118 may reinforce a rigidity of the first frame 110. The first ribs 117 and 118 include a first main rib 117 provided in a longitudinal direction of the first frame 110, and a first sub-rib 118 provided in a direction intersecting a longitudinal direction of the first main rib 117. The first main rib 117 may be disposed along a longitudinal edge of the first frame 110. The first sub-rib 118 may be provided in a direction orthogonal to the first main rib 117.

The second frame 120 may be coupled or connected to the first frame 110 and the applying member 54 of FIG. 2. The second frame 120 includes an extending portion 122, an applying portion 123, a second guide portion 124, and second ribs 127 and 128. The second frame 120 may be in surface contact with a portion of the object.

The second guide portion 124 may be slidingly connected to the first guide portion 112. The second guide portion 124 and the first guide portion 112 may function as passive joints that enable a rectilinear motion. The second guide portion 124 may slidingly move and coupled to the first guide portion 112 in a direction intersecting the hinge axis of the hinge connecting portion 114. For example, the second guide portion 124 may slidingly move in a direction perpendicular to the hinge axis of the hinge connecting portion 114. The second guide portion 124 may be in surface contact with a portion of the object. A cross-section of the second guide portion 124 taken in the direction of the hinge axis of the hinge connecting portion 114 may be elongated in the direction of the hinge axis of the hinge connecting portion 114 of the first guide portion 112.

The second guide portion 124 includes a guide recess 125 into which the first guide portion 112 is to be inserted or from which the first guide portion 112 is to be pulled out, and a guide cover 126 covering the guide recess 125. The guide recess 125 may have a shape corresponding to a shape of the first guide portion 112.

The applying portion 123 may be connected to the applying member 54 to apply the assistance force to the thigh of the object. The applying portion 123 may be disposed on a front surface of the thigh of the object. The applying portion 123 may include a face provided in a direction intersecting the hinge axis of the hinge connecting portion 114 of the first guide portion 112. For example, the applying portion 123 may include a face provided in a direction orthogonal to the hinge axis of the hinge connecting portion 114 of the first guide portion 112. For example, the applying portion 123 may include a face parallel to a slidingly moving direction of the first guide portion 112 and the second guide portion 124. That is, the applying portion 123 may include a face orthogonal to a face of the second guide portion 124.

The extending portion 122 may couple or connect the second guide portion 124 to the applying portion 123. The extending portion 122 may have a gradually twisted shape from the second guide portion 124 to the applying portion 123. For example, the extending portion 122 may be gradually twisted such that a surface of the extending portion 122 adjacent to the second guide portion 124 and a surface of the extending portion 122 adjacent to the applying portion form 90 degrees.

The second ribs 127 and 128 may reinforce a rigidity of the second frame 120. The second ribs 127 and 128 include a second main rib 128 provided in a longitudinal direction of the second frame 120, and a second sub-rib 127 provided in a direction intersecting a longitudinal direction of the second main rib 128. For example, the second main rib 128 may be disposed along a longitudinal edge of the second frame 120. The second sub-rib 127 may be provided in a direction orthogonal to the second main rib 128.

The assistance force sensing portion 130 of FIG. 5 may measure a tensile force applied to a frame. The assistance force sensing portion 130 may be disposed on at least one of the first frame 110 and the second frame 120. Hereinafter, a case in which the assistance force sensing portion 130 is disposed on the first frame 110 will be described. The assistance force sensing portion 130 includes a tensile force measuring sensor 132, a deformed recess 134, and a sensor disposition space 136.

The sensor disposition space 136 may provide a space in which the tensile force measuring sensor 132 is to be disposed. The sensor disposition space 136 may be a space recessed from one surface of the first frame 110. The sensor disposition space 136 may be a space defined between the first main rib 117 and the first sub-rib 118. The sensor disposition space 136 may also be a hole defined in the first frame 110. Through the aforementioned structure, damage to the tensile force measuring sensor 132, which results from friction between the tensile force measuring sensor 132 and at least one of the first frame 110 and the second frame 120, may be prevented or mitigated.

The sensor disposition space 136 may not be provided. In the case that the sensor disposition space 136 is not provided, the tensile force measuring sensor 132 may be disposed on, for example, an upper surface or a lower surface of the first frame 110.

The tensile force measuring sensor 132 may sense a tensile force applied to a portion to which the tensile force measuring sensor 132 is attached. For example, a strain gauge may be used as the tensile force measuring sensor 132. The tensile force measuring sensor 132 may measure a tensile force applied in the longitudinal direction of the first frame 110. The strain gauge may be disposed lengthwise in the slidingly moving direction of the first frame 110 and the second frame 120. A plurality of tensile force measuring sensors 132 may be provided. The tensile force measuring sensors 132 may be disposed on an upper side and a lower side of the first frame 110, respectively. The tensile force measuring sensors 132 may be disposed in a symmetric manner. At least some pairs of the plurality of tensile force measuring sensors 132 may be disposed to face each other in up and down directions as illustrated in FIG. 4. Some of the tensile force measuring sensors 132 may be disposed to face each other in a motion direction of the thigh of the object. Some of the tensile force measuring sensors 132 may be disposed to face each other in a direction of the assistance force. For example, the tensile force measuring sensors 132 may be attached to walls of the sensor disposition space 136.

The deformed recess 134 may increase a flexibility of a desired (or alternatively, predetermined) portion of the first frame 110. The deformed recess 134 may be provided on a portion at which the tensile force measuring sensor 132 is to be disposed. The deformed recess 134 may be disposed to overlap the tensile force measuring sensor 132 in the direction of the assistance force. By means of the deformed recess 134, the tensile force measuring sensor 132 may sensitively respond to a change in the assistance force. Thus, a sensitivity of the tensile force measuring sensor 132 may increase. Thus, a resolution of the tensile force measuring sensor 132 may increase, and the assistance force may be measured with improved accuracy. A plurality of deformed recesses 134 may be provided. A number of the deformed recesses 134 may correspond to a number of the tensile force measuring sensors 132. The deformed recesses 134 may be provided at an upper end and a lower end of the first frame 110. The deformed recesses 134 may be provided on the first main rib 117.

Hereinafter, an operation of the assistance force sensing portion 130 will be described.

The supporting frame 100 may rotate in a rotating direction of the joint member 40 to transmit a force to a portion of the object supported by the supporting frame 100. According to the action-reaction law, a magnitude of a force applied to a portion of the object may be measured by measuring a force applied to the supporting frame 100. The force applied to the supporting frame 100 may be classified into forces Fx, Fy, and Fz of three axial directions and moments Mx, My, and Mz of the three axial directions, as shown in FIG. 3. In an x-y-z coordinate system of FIG. 3, a direction of the assistance force to rotate the object may be matched to a z axis, and the assistance force may be Fz. The remaining forces, excluding Fz, and the moments may be referred to as disturbances. Hereinafter, effects of the disturbances Fx, Fy, Mx, My, and Mz on the assistance force sensing portion 130 will be described as follows.

The force Fx may not be applied to the supporting frame 100 when the hinge connecting portion 114 is rotatably connected to the joint member 40. By means of a rotary passive joint, an effect of the force Fx on the assistance force sensing portion 130 may be substantially eliminated.

The force Fy may not be applied to the supporting frame 100 when the first frame 110 and the second frame 120 are disposed to slidingly move in a y-axial direction. By means of a sliding passive joint, an effect of the force Fy on the assistance force sensing portion 130 may be substantially eliminated.

The moment Mx may be substantially eliminated by an operation of the controller 70. The moment Mx may correspond to a bending moment applied to the supporting frame 100. By disposing the tensile force measuring sensors 132 on the upper side and the lower side of the first frame 110, respectively, and comparing values measured by the tensile force measuring sensors 132, an effect of the bending moment Mx on the assistance force sensing portion 130 may be measured. This measured effect of the bending moment Mx may be substantially eliminated using the controller 70.

Meanwhile, when the supporting frame 100 is disposed between two joints, a portion of the object to be connected between the joints may perform a rigid body motion, and Thus, the moment Mx may not be actually applied. For example, when one side of the supporting module 50 of FIG. 1 is connected to a hip joint of the object, and another side of the supporting module 50 is connected to a thigh of the object, the moment Mx may not be actually applied.

The moment My may be ignored. The moment My may correspond to a twisting moment applied to the supporting frame 100. The twisting moment My may not cause a change in a length in a y-axial direction of the supporting frame 100. Thus, a tensile force applied by the twisting moment My in the y-axial direction of the supporting frame 100 may be considered negligible.

The moment Mz may not be applied to the supporting frame 100 when the hinge connecting portion 114 is rotatably connected to the joint member 40. By means of a rotary passive joint, an effect of the moment Mz on the assistance force sensing portion 130 may be prevented or mitigated.

Thus, according to example embodiments, the disturbances may be eliminated, and the assistance force Fz may be accurately measured.

FIG. 5 is a perspective view illustrating a deformation of the supporting frame 100 according to example embodiments. FIG. 5 illustrates the first frame 110 deformed when a portion of an object is pulled by the first frame 110 of the supporting frame 100. In this example, it may be assumed that the moment Mx of FIG. 3 is not applied.

A portion of the first frame 110 on which a deformed recess 134 is provided may be deformed with relative ease. Further, applications disturbances other than Fz may be prevented or mitigated. Thus, when deformed recesses 134 are provided on an upper side and a lower side of the first frame 110, respectively, to face each other, portions of the first frame 110 on which the deformed recesses 134 are provided may be deformed in a parallelogram shape, as shown in FIG. 5. Accordingly, both end portions of the first frame 110 may not differ in angles, but may differ in heights. Thus, an angle of rotation of the portion of the object and an angle of rotation of the joint member 40 may match. Thus, an actual angle at which the portion of the object rotates may be accurately measured using the encoder (now shown) on one side of the joint member 40 of FIG. 1.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 6:
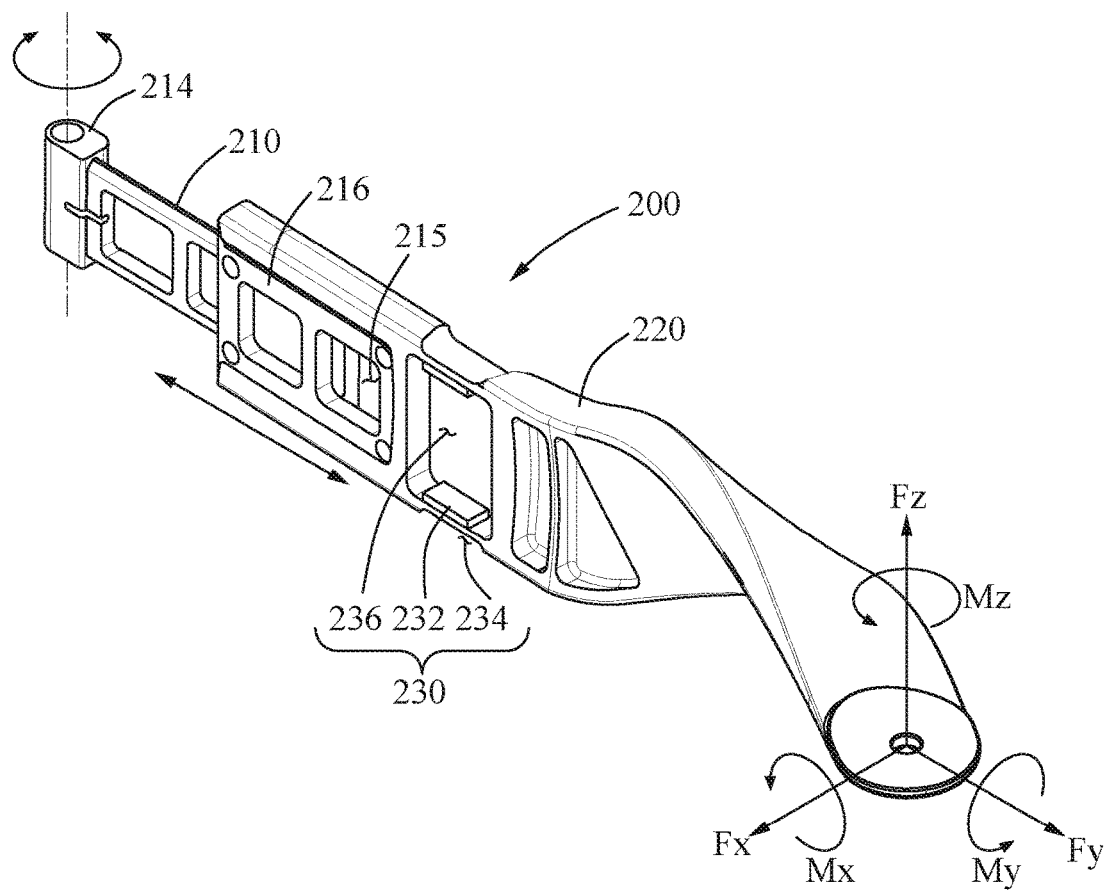
FIG. 6 is a perspective view illustrating a supporting frame according to example embodiments.

FIG. 6 is a perspective view illustrating a supporting frame 200 according to example embodiments. FIG. 6 illustrates an example of an assistance force sensing portion 230 disposed on a second frame 220.

Referring to FIG. 6, the supporting frame 200 includes a first frame 210, the second frame 220, and the assistance force sensing portion 230. The first frame 210 includes a hinge coupling portion 214 to be coupled or connected to the joint member 40 of FIG. 1. The second frame 220 includes a guide recess 215 to guide and accommodate the first frame 210, and a guide cover 216 to cover the guide recess 215.

The assistance force sensing portion 230 includes a tensile force measuring sensor 232 to measure a tensile force applied to the second frame 220, a deformed recess 234 to increase a sensitivity of the tensile force measuring sensor 232, and a sensor disposition space 236 provided to be recessed from one side of the second frame 220.

Figure 7:
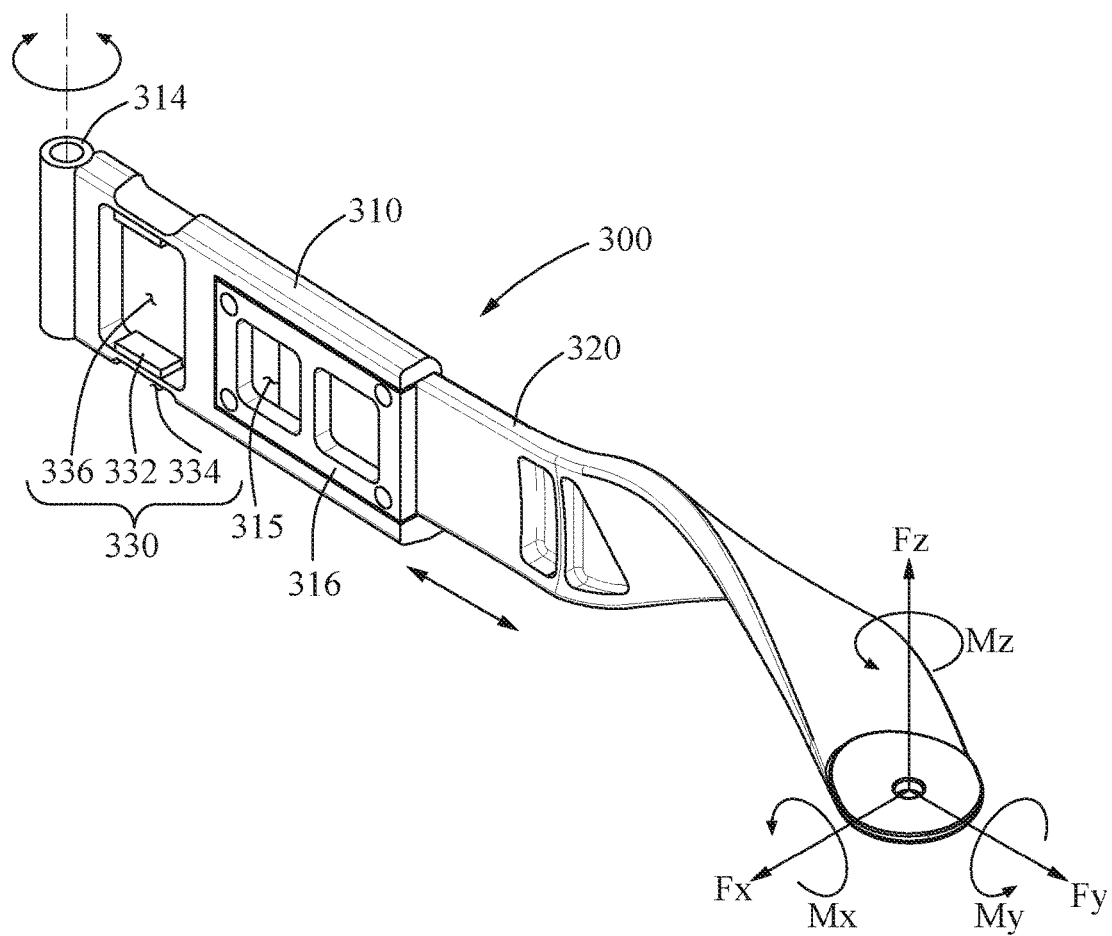
FIG. 7 is a perspective view illustrating a supporting frame according to example embodiments.

FIG. 7 is a perspective view illustrating a supporting frame 300 according to example embodiments. FIG. 7 illustrates an example of a guide recess 315 and a guide cover 316 provided in a first frame 310.

Referring to FIG. 7, the supporting frame 300 includes the first frame 310, a second frame 320, and an assistance force sensing portion 330. The first frame 310 includes a hinge connecting portion 314 to be connected to the joint member 40 of FIG. 1. The first frame 310 further includes the guide recess 315 to guide and accommodate the second frame 320, and the guide cover 316 to cover the guide recess 315.

The assistance force sensing portion 330 includes a tensile force measuring sensor 332 to measure a tensile force applied to the first frame 310, a deformed recess 334 to increase a sensitivity of the tensile force measuring sensor 332, and a sensor disposition space 336 provided to be recessed from one side of the first frame 310.

Figure 8:
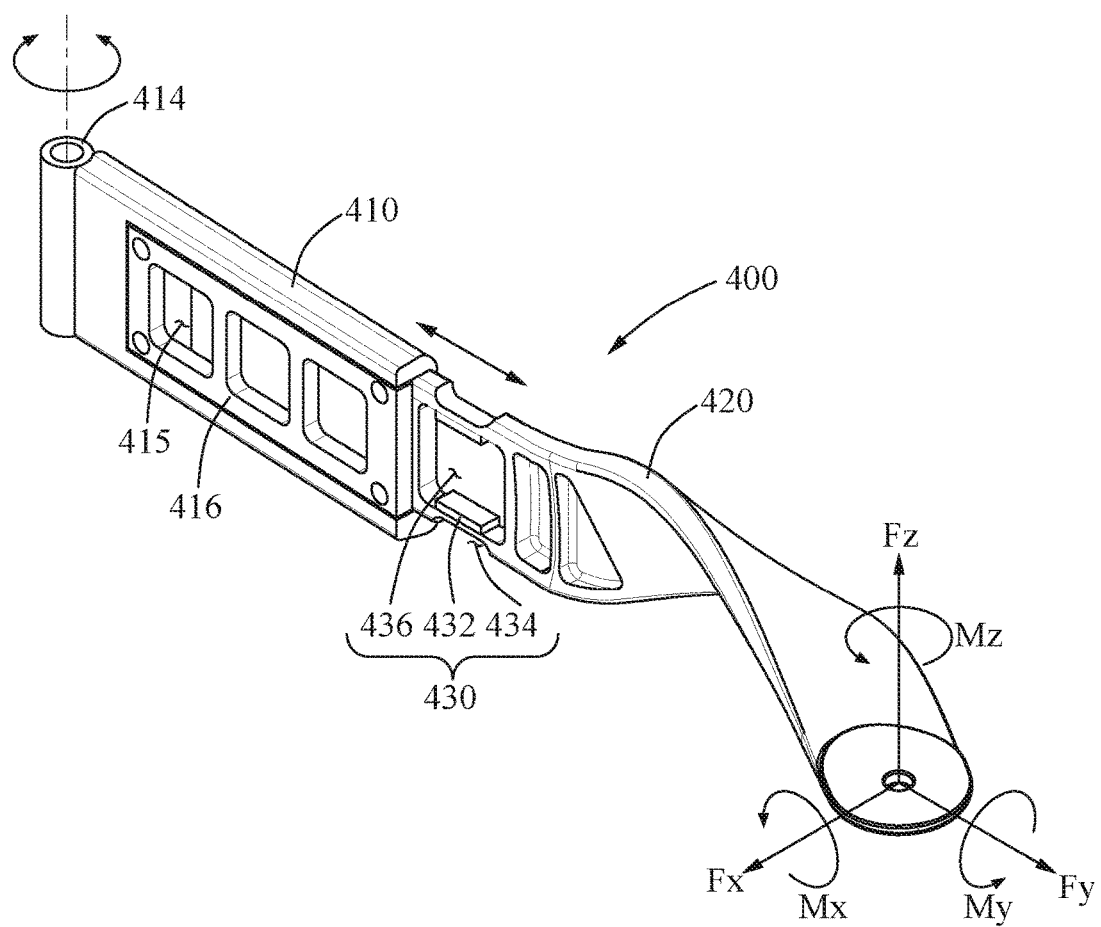
FIG. 8 is a perspective view illustrating a supporting frame according to example embodiments.

FIG. 8 is a perspective view illustrating a supporting frame 400 according to example embodiments. FIG. 8 illustrates an example of an assistance force sensing portion 430 being disposed on a second frame 420, and a guide recess 415 and a guide cover 416 being provided in a first frame 410. Detailed descriptions thereof will be omitted for conciseness.

Figure 9:
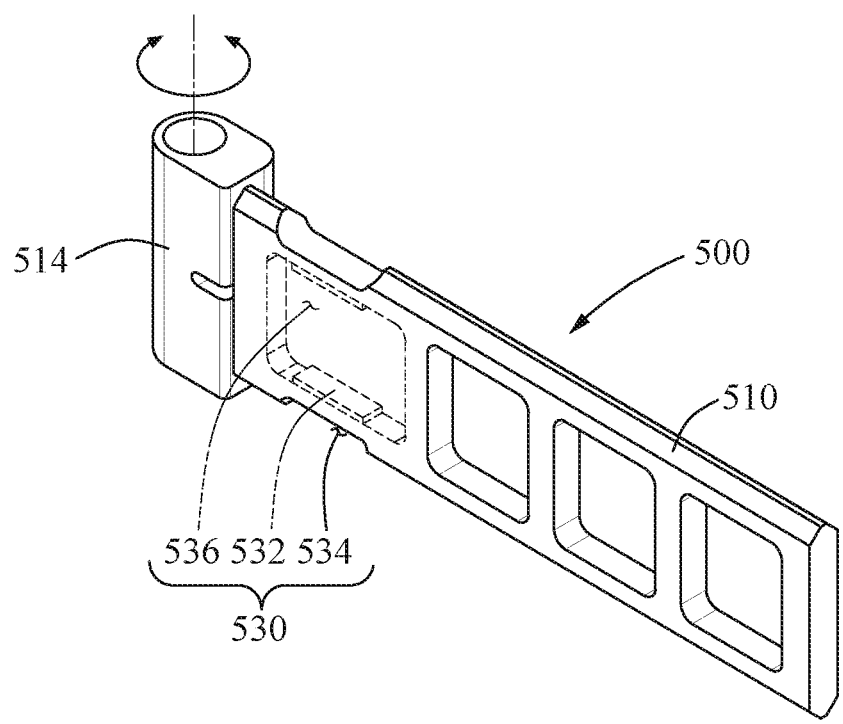
FIG. 9 is a perspective view illustrating a supporting frame according to example embodiments.

FIG. 9 is a perspective view illustrating a supporting frame 500 according to example embodiments.

Referring to FIG. 9, the supporting frame 500 includes a first frame 510, a second frame (not shown), and an assistance force sensing portion 530. The assistance force sensing portion 530 includes a tensile force measuring sensor 532, a deformed recess 534, and a sensor disposition space 536.

The sensor disposition space 536 may be provided in an internal portion of the first frame 510. In this example, damage to the tensile force measuring sensor 532 resulting from an impact applied from an outer side may be prevented or mitigated. The assistance force sensing portion 530 may also be disposed in the second frame.

Figure 10:
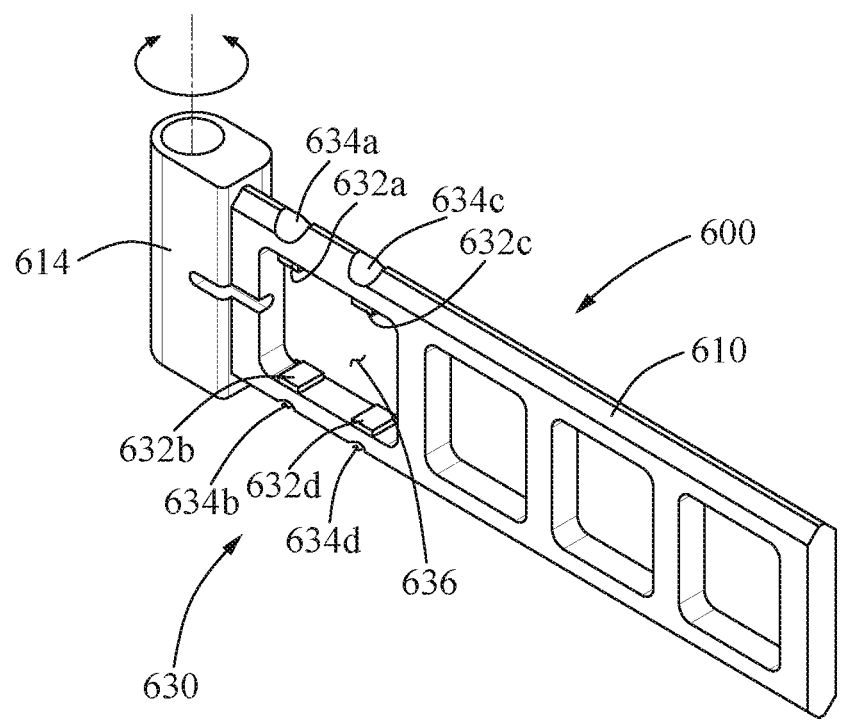
FIG. 10 is a perspective view illustrating a supporting frame according to example embodiments.

FIG. 10 is a perspective view illustrating a supporting frame 600 according to example embodiments.

Referring to FIG. 10, the supporting frame 600 includes a first frame 610, a second frame (not shown), and an assistance force sensing portion 630. The assistance force sensing portion 630 includes a tensile force measuring sensors 632a to 632d, a deformed recess 634, and a sensor disposition space 636.

The tensile force measuring sensors 632a to 632d includes two pairs of tensile force measuring sensors, two tensile force measuring sensors of each of which are disposed to face each other in a direction of an assistance force. A first tensile force measuring sensor 632a and a second tensile force measuring sensor 632b may be disposed to face each other in the direction of the assistance force, and a third tensile force measuring sensor 632c and a fourth tensile force measuring sensor 632d may be disposed to face each other in the direction of the assistance force.

A plurality of tensile force measuring sensors 632a to 632d may be disposed in a direction orthogonal to the direction of the assistance force. The plurality of tensile force measuring sensors 632 may be disposed in a longitudinal direction of the first frame 610. The first tensile force measuring sensor 632a and the third tensile force measuring sensor 632c may be disposed to be spaced apart from each other in the longitudinal direction of the first frame 610, and the second tensile force measuring sensor 632b and the fourth tensile force measuring sensor 632d may be disposed to be spaced apart from each other in the longitudinal direction of the first frame 610.

A plurality of deformed recesses 634a to 634d, including a first deformed recess 634a, a second deformed recess 634b, a third deformed recess 634c, and a fourth deformed recess 634d, may be provided to correspond to the plurality of tensile force measuring sensors 632, respectively. The assistance force sensing portion 630 may also be disposed in the second frame.

Figure 11:
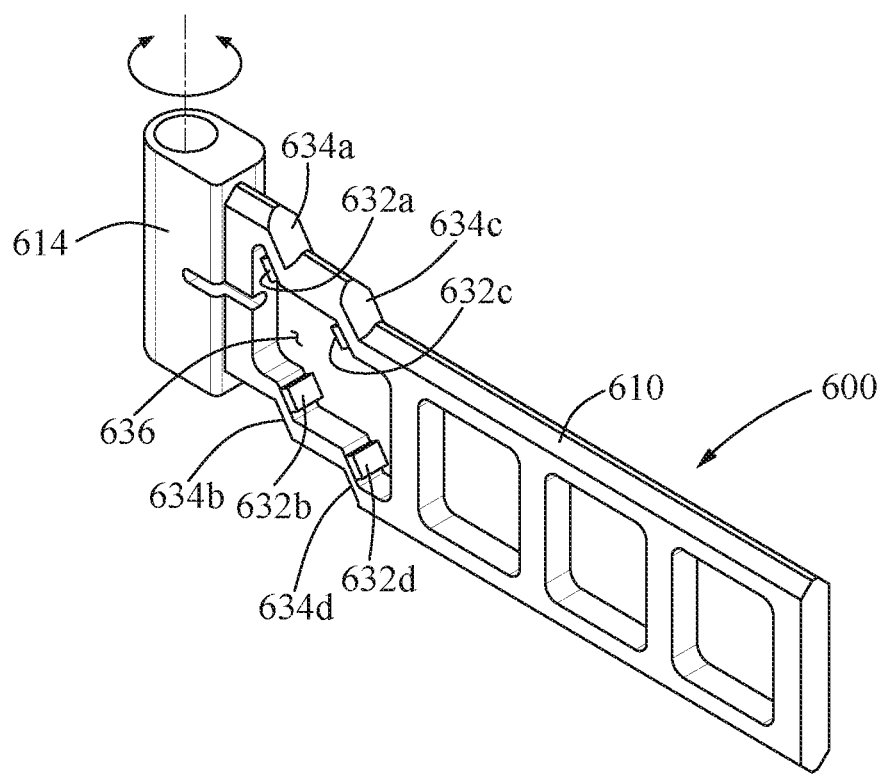
FIG. 11 is a perspective view illustrating a deformation of a supporting frame according to example embodiments.

FIG. 11 is a perspective view illustrating a deformation of the supporting frame 600 according to example embodiments. FIG. 11 illustrates the first frame 610 deformed when a portion of an object is pulled by the first frame 610 of the supporting frame 600. In this example, it may be assumed that the moment Mx of FIG. 3 is not applied.

Portions of the first frame 610 on which the deformed recesses 634 are provided may be deformed in a shape of a plurality of parallelograms, as shown in FIG. 11.

According to some example embodiments, the controller 70, as shown in FIG. 2, may include a processor and/or a memory.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform motion assisting operation such that the processor is configured to control the driving module 30 to assist a motion of an object.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

A number of example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A supporting frame comprising:
   a first frame including a hinge connecting portion;
   a second frame configured to slidingly move with respect to the first frame in a continuous manner while the supporting frame is worn by a user;
   an assistance force sensing portion on at least one of the first frame and the second frame, the assistance force sensing portion including at least one pair of a first strain gauge and a second strain gauge, the at least one pair of the first strain gauge and the second strain gauge provided to face each other in at least one sensor disposition space defined in at least one of the first frame or the second frame; and
   a controller configured to eliminate an effect of a bending moment applied to the supporting frame based on values measured by the at least one pair of the first strain gauge and the second strain gauge.

2. The supporting frame of claim 1, wherein a slidingly moving direction of the second frame intersects a hinge axis of the hinge connecting portion of the first frame.

3. The supporting frame of claim 2, wherein the assistance force sensing portion comprises a first strain gauge disposed lengthwise in the slidingly moving direction of the second frame.

4. The supporting frame of claim 3, wherein the assistance force sensing portion comprises at least one pair of the first strain gauge and the second strain gauge disposed on an upper side and a lower side of the first frame, respectively, or disposed on an upper side and a lower side of the second frame, respectively.

5. The supporting frame of claim 2, wherein at least one of a cross-section of the first frame and a cross-section of the second frame taken in a direction of the hinge axis of the hinge connecting portion is elongated in the direction of the hinge axis of the hinge connecting portion.

6. The supporting frame of claim 5, wherein a portion of the at least one of the first frame and the second frame, on which the at least one pair of the first strain gauge and the second strain gauge is disposed, has a height in the direction of the hinge axis smaller than that of a remaining portion of the at least one of the first frame and the second frame.

7. The supporting frame of claim 6, wherein the at least one of the first frame and the second frame includes a deformed recess defined therein to accommodate the at least one pair of the first strain gauge and the second strain gauge.

8. The supporting frame of claim 1, wherein the second frame comprises:
   a second guide portion configured to slidingly couple to a first guide portion of the first frame;
   an extending portion extending from the second guide portion; and
   an applying portion extending from the extending portion and configured to transmit an assistance force to an object.

9. The supporting frame of claim 8, wherein the applying portion includes a face orthogonal to a hinge axis of the hinge connecting portion.

10. The supporting frame of claim 8, wherein the applying portion includes a face parallel to a slidingly moving direction of the first guide portion and the second guide portion.

11. The supporting frame of claim 8, wherein the applying portion comprises a face orthogonal to a face of the second guide portion.

12. A supporting frame for transmitting power to an object, the supporting frame comprising:
- a first frame including a hinge connecting portion, the hinge connecting portion configured to rotate on an axis corresponding to a power transmitting direction of the supporting frame;
- a second frame configured to slidingly move with respect to the first frame in a direction intersecting the power transmitting direction in a continuous manner while the supporting frame is worn by a user;
- at least one pair of a first tensile force measuring sensor and a second tensile force measuring sensor, the at least one pair of the first tensile force measuring sensor and the second tensile force measuring sensor provided to face each other in at least one sensor disposition space defined in at least one of the first frame or the second frame; and
- a controller configured to eliminate an effect of a bending moment applied to the supporting frame based on values measured by the at least one pair of the first tensile force measuring sensor and the second tensile force measuring sensor.

13. The supporting frame of claim 12, wherein the at least one pair of the first tensile force measuring sensor and the second tensile force measuring sensor includes a plurality of pairs of tensile force measuring sensors, and
- at least one pair of the plurality of pairs of tensile force measuring sensors are disposed to face each other in the power transmitting direction.

14. The supporting frame of claim 13, wherein the at least one pair of the first tensile force measuring sensor and the second tensile force measuring sensor includes two pairs of tensile force measuring sensors disposed to face each other in the power transmitting direction.

15. The supporting frame of claim 12, wherein the at least one of the first frame and the second frame includes a deformation resistant rib.

16. The supporting frame of claim 15, wherein the deformation resistant rib includes a deformed recess defined therein, and
- the at least one pair of the first tensile force measuring sensor and the second tensile force measuring sensor is disposed to overlap the deformed recess in the power transmitting direction.

17. A motion assistance apparatus comprising:
- a fixing member configured to be fixed to an object;
- a driving module on one side of the fixing member;
- a joint member rotatably connected to the fixing member, the joint member configured to be driven by the driving module;
- a first frame rotatably coupled to the joint member;
- a second frame configured to slidingly couple to the first frame in a continuous manner while the motion assistance apparatus is worn by a user;
- a supporting member coupled to the second frame to support a portion of the object;
- at least one pair of a first tensile force measuring sensor and a second tensile force measuring sensor, the at least one pair of the first tensile force measuring sensor and the second tensile force measuring sensor provided to face each other in at least one sensor disposition space defined in at least one of the first frame or the second frame; and
- a controller configured to eliminate an effect of a bending moment applied to the motion assistance apparatus based on values measured by the at least one pair of the first tensile force measuring sensor and the second tensile force measuring sensor.

18. The motion assistance apparatus of claim 17, wherein an axis of rotation of the first frame is orthogonal to an axis of rotation of the joint member.

19. The motion assistance apparatus of claim 17, wherein a slidingly moving direction of the first frame and the second frame is orthogonal to an axis of rotation of the joint member.

20. The motion assistance apparatus of claim 17, further comprising:
- an encoder configured to measure an angle of rotation of the joint member,
- wherein deformed recesses are provided to be symmetric with respect to each other on an upper side and a lower side of the at least one of the first frame and the second frame, respectively.

* * * * *